US011331317B2

(12) United States Patent
Lee et al.

(10) Patent No.: US 11,331,317 B2
(45) Date of Patent: May 17, 2022

(54) COMPOSITION FOR TREATING VASCULAR OR CARDIAC VALVULAR CALCIFICATION, CONTAINING THIAMINE DERIVATIVE

(71) Applicant: KYUNGPOOK NATIONAL UNIVERSITY INDUSTRY-ACADEMIC COOPERATION FOUNDATION, Daegu (KR)

(72) Inventors: In Kyu Lee, Daegu (KR); Jae Han Jeon, Daegu (KR); Chang Joo Oh, Daegu (KR); Ji Min Lee, Daegu (KR)

(73) Assignee: KYUNGPOOK NATIONAL UNIVERSITY INDUSTRY-ACADEMIC COOPERATION FOUNDATION, Daegu (KR)

(*) Notice: Subject to any disclaimer, the term of this patent is extended or adjusted under 35 U.S.C. 154(b) by 0 days.

(21) Appl. No.: 17/266,459

(22) PCT Filed: Jul. 22, 2019

(86) PCT No.: PCT/KR2019/009015
§ 371 (c)(1),
(2) Date: Feb. 5, 2021

(87) PCT Pub. No.: WO2020/032426
PCT Pub. Date: Feb. 13, 2020

(65) Prior Publication Data
US 2021/0290621 A1  Sep. 23, 2021

(30) Foreign Application Priority Data

Aug. 7, 2018 (KR) .................. 10-2018-0092019
Jul. 19, 2019 (KR) .................. 10-2019-0087554

(51) Int. Cl.
| | | |
|---|---|---|
| *A61K 31/506* | (2006.01) | |
| *A61K 31/505* | (2006.01) | |
| *A23L 33/15* | (2016.01) | |
| *A61P 3/14* | (2006.01) | |
| *A61P 9/14* | (2006.01) | |
| *A23L 33/00* | (2016.01) | |

(52) U.S. Cl.
CPC ............ *A61K 31/506* (2013.01); *A23L 33/15* (2016.08); *A23L 33/40* (2016.08); *A61K 31/505* (2013.01); *A61P 3/14* (2018.01); *A61P 9/14* (2018.01); *A23V 2002/00* (2013.01)

(58) Field of Classification Search
CPC ..... A61K 31/506; A61K 31/505; A23L 33/15; A23L 33/40; A61P 3/14; A61P 9/14; A23V 2002/00
See application file for complete search history.

(56) References Cited

U.S. PATENT DOCUMENTS 3,872,123 A * 3/1975 Takamizawa ........ C07D 415/00
544/296
2015/0065693 A1  3/2015 Song et al.

FOREIGN PATENT DOCUMENTS

CN  105147708 A  12/2015
EP  0820770 A2  1/1998

OTHER PUBLICATIONS

Abedin et al., "Vascular calcification: mechanisms and clinical ramifications," Arterioscler. Thromb. Vasc. Biol. 24(7):1161-1170 (2004).
Barrett et al., "Diabetic microvascular disease: an endocrine society scientific statement," J. Clin. Endocrinol. Metab. 102(12):4343-4410 (2017).
Lee et al., "The preventive effect of fursulthiamine on dietary hypertension in rats," J. Pharm. Soc. Korea, Yakhak Hoeji, 43(1):91-97 (1999).
Nicoll et al., "Cardiovascular calcification and bone: a comparison of the effects of homocysteine and dietary and serum B vitamins," Ann. Vasc. Med. Res. 4(4):1065 (2017) (10 pages).
Raj et al., "Therapeutic potential of benfotiamine and its molecular targets," Eur. Rev. Med. Pharm. Sci. 22(10):3261-3273 (2018).
Extended European Search Report dated Sep. 10, 2021 for European Patent Application No. 19846789.6 (5 pages).
Lee et al., "Vascular Calcification—New Insights into Its Mechanism," Int. J. Mol. Sci. 21(8):1-32 (2020).

* cited by examiner

*Primary Examiner* — Timothy R Rozof
(74) *Attorney, Agent, or Firm* — Clark & Elbing LLP; Susan M. Michaud

(57) ABSTRACT

The present invention relates to: a pharmaceutical composition for preventing or treating vascular or cardiac valvular calcification, containing a thiamine derivative or a pharmaceutically acceptable salt thereof; and a food composition for alleviating vascular or cardiac valvular calcification, containing a thiamine derivative or a salt thereof, and the compositions of the present invention can be effectively used for a use of preventing, treating or alleviating vascular or cardiac valvular calcification.

5 Claims, 4 Drawing Sheets

COMPOSITION FOR TREATING VASCULAR OR CARDIAC VALVULAR CALCIFICATION, CONTAINING THIAMINE DERIVATIVE

TECHNICAL FIELD

The present disclosure relates to a composition for preventing, alleviating, or treating vascular or valvular calcification and, specifically, to a composition containing a thiamine derivative for preventing, alleviating, or treating vascular or valvular calcification.

The present disclosure is made with the support of the Ministry of Science and ICT, Republic of Korea, under Project No. NRF-2017R1A2B3006406, which was conducted in the research project named "New Therapeutic Mechanism of Chronic Inflammation and Metabolic Syndrome through Mitochondria-Associated ER Membrane (MAM) Interaction and Pyruvate Dehydrogenase Kinase (PDK) Activity Regulation" in the research program titled "Mid-Career Research", by the Kyungpook National University Glocal Industry-Academic Cooperation Foundation, under management of the National Research Foundation of Korea, from 1 Mar. 2017 to 28 Feb. 2022. The present disclosure was also made with the support of the Ministry of Health and Welfare, Republic of Korea, under Project No. HI16C1501, which was conducted in the research project named "Leading-edge Research Center for Drug Discovery and Development for Diabetes and Metabolic Disease" in the research program titled "Leading Characterization Research Program", by the Kyungpook National University Hospital, under management of the Korea Health Industry Development Institute, from 1 Apr. 2016 to 31 Mar. 2021.

This application claims priorities to and the benefits of Korean Patent Application Nos. 10-2018-0092019 and 10-2019-0087554, filed in the Korean Intellectual Property Office on 7 Aug. 2018 and 19 Jul. 2019, respectively, the disclosures of which are incorporated herein by reference.

BACKGROUND ART

Blood vessels, which are circulatory organs that continuously regulate the movement of body fluids, function to supply oxygen, nutrients, and the like to tissues and receive carbon dioxide or wastes from the tissues.

Vascular calcification is the deposition of minerals, such as calcium and phosphate, in blood vessels, and causes the rupture of blood vessels by increasing vascular stiffness. This vascular calcification is commonly found in patients with arteriosclerosis, diabetes, and chronic renal failure, and the loss of calcium accumulation suppression mechanisms, the induction of bone formation, nucleation complexes in blood, apoptosis, and the like are reported to be main causes of vascular calcification, but accurate mechanisms thereof have still not been revealed.

Especially, cardiovascular calcification contributes to exacerbation of valvular diseases, such as hypertension, heart failure, and acute coronary artery syndrome, and causes several complications (e. g., sudden cardiac death, myocardial infarction, angina, and ischemic heart failure, etc.) resulting therefrom. However, the accurate mechanisms of vascular calcification have not yet been revealed as mentioned above, and thus agents for preventing and treating vascular calcification have not yet been developed.

Therefore, the development of techniques with respect to a composition for preventing, alleviating, or treating vascular or valvular calcification is urgent.

DETAILED DESCRIPTION OF THE INVENTION

Technical Problem

The present inventors have made an extensive research effort to develop a composition for preventing, alleviating, or treating vascular or valvular calcification. As a result, the present inventors established that a thiamine derivative has a vascular calcification inhibitory effect, and therefore completed the present disclosure.

Accordingly, an aspect of the present invention is to provide a pharmaceutical composition containing a thiamine derivative or a pharmaceutically acceptable salt thereof for preventing or treating vascular or valvular calcification.

Another aspect of the present invention is to provide a food composition containing a thiamine derivative or a salt thereof for preventing or treating vascular or valvular calcification.

Still another aspect of the present invention is to provide a method for preventing or treating vascular or valvular calcification, the method including a step of administering to an individual a pharmaceutical composition containing a thiamine derivative or a pharmaceutically acceptable salt thereof.

Still another aspect of the present invention is to provide a use of a pharmaceutical composition for the treatment of vascular or valvular calcification, the pharmaceutical composition containing a thiamine derivative or a pharmaceutically acceptable salt thereof.

Technical Solution

The present inventors have made an extensive research effort to develop a composition for preventing, alleviating, or treating vascular or valvular calcification. As a result, the present inventors have established that a thiamine derivative has a vascular calcification inhibitory effect.

The present disclosure is directed to: a pharmaceutical composition containing a thiamine derivative or a pharmaceutically acceptable salt thereof for preventing or treating vascular or valvular calcification; a food composition containing a thiamine derivative or a salt thereof for alleviating vascular or valvular calcification; a method for preventing/treating vascular or valvular calcification by using a pharmaceutical composition containing a thiamine derivative or a pharmaceutically acceptable salt thereof; and a use thereof for the treatment of vascular or valvular calcification.

Hereinafter, the present disclosure will be described in more detail.

In accordance with an aspect of the present invention, there is provided a pharmaceutical composition containing a thiamine derivative represented by chemical formula 1 below and a pharmaceutically acceptable salt thereof for preventing or treating vascular or valvular calcification:

[Chemical Formula 1]

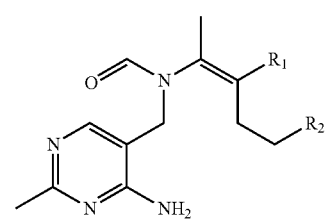

wherein, $R_1$ is any one selected from the group consisting of

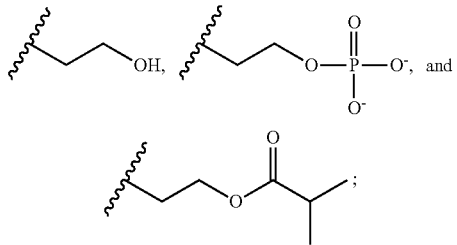

and $R_2$ is any one selected from the group consisting of

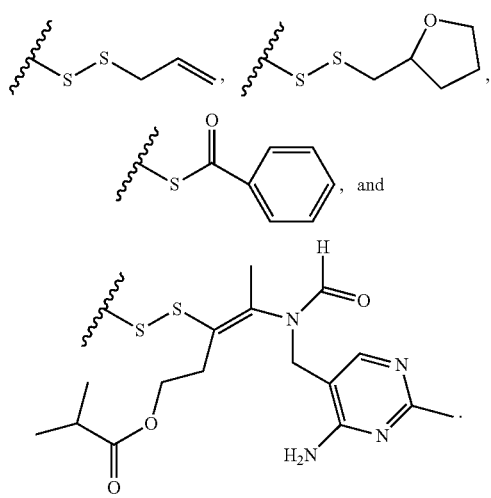

In an embodiment of the present disclosure, $R_1$ may be

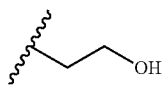 [SMILES: *CCO]

and $R_2$ may be

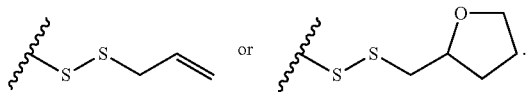

When $R_1$ is

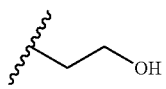 [SMILES: *CCO]

and $R_2$ is

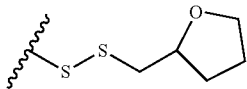 [SMILES: *SSCC1CCCO1]

in chemical formula 1, the thiamine derivative is fursultiamine (thiamine tetrahydrofurfuryl disulfide).

When $R_1$ is

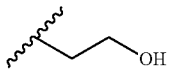 [SMILES: *CCO]

and $R_2$ is

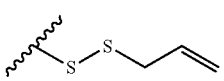 [SMILES: *SSCC=C]

in chemical formula 1, the thiamine derivative is allithiamine (thiamine allyl disulfide).

When $R_1$ is

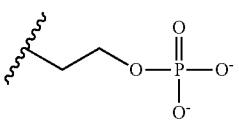 [SMILES: *CCOP(=O)([O-])[O-]]

and $R_2$ is

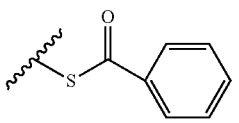 [SMILES: *SC(=O)c1ccccc1]

in chemical formula 1, the thiamine derivative is benfotiamine (S-benzoylthiamine O-monophosphate).

When $R_1$ is

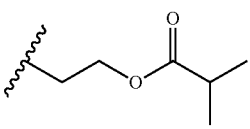 [SMILES: *CCOC(=O)C(C)C]

and $R_2$ is

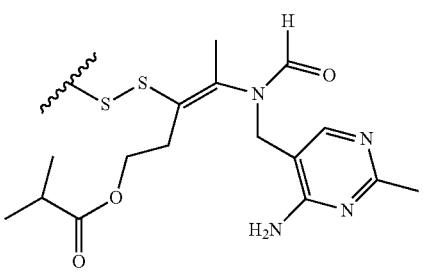 [SMILES: *SS/C(CCOC(=O)C(C)C)=C(\C)N(C=O)Cc1cnc(C)nc1N]

in chemical formula 1, the thiamine derivative is sulbutiamine (O-isobutyrylthiamine disulfide).

Herein, the thiamine derivative is directly absorbed in the small intestine due to fat-soluble properties thereof, and thus shows high bio-availability in the liver, muscle, nerve tissues, and the like.

As used herein, the term "derivative" refers to a compound which is obtained by chemically changing a part of a compound, used as a parent moiety, through the introduction of functional groups, oxidation, reduction, substitution of atoms, or the like of a functional group, and the derivative is a similar compound obtained from the change of the parent compound to the extent that the structure and properties of the parent compound are not drastically changed. Usually, the derivative refers to a compound in which a hydrogen atom or a specific atom group of a compound is replaced by another atom or atom group.

As used herein, the term "vascular or valvular calcification" refers to the formation, growth, or deposition of extracellular matrix hydroxyapatite (calcium phosphate) crystal deposits in the blood vessel or valves.

The vascular or valvular calcification may be caused by a valvular disease, hyperlipidemia, aging, estrogen deficiency, angina, heart failure, a kidney disease, uremia, diabetes, an inflammatory disease, or a cardiovascular disease.

An example of the kidney disease may be glomerulonephritis, diabetic nephritis, lupus nephritis, polycystic kidney disease, pyelonephritis, lithonephria, nephrotuberculosis, or a renal tumor.

An example of the inflammatory disease is asthma, allergic and non-allergic rhinitis, chronic and acute rhinitis, chronic and acute gastritis or enteritis, ulcerative gastritis, acute and chronic nephritis, acute and chronic hepatitis, chronic obstructive pulmonary disease, pulmonary fibrosis, irritable bowel syndrome, inflammatory pain, migraine, headache, back pain, fibromyalgia, myofascial disease, viral infections (e.g., type C infection), bacterial infections, fungal infections, burns, wounds by surgical or dental surgery, hyperprostaglandin E syndrome, atherosclerosis, gout, arthritis, rheumatoid arthritis, ankylosing spondylitis, Hodgkin's disease, pancreatitis, conjunctivitis, iritis, scleritis, uveitis, dermatitis, eczema, or multiple sclerosis.

An example of the cardiovascular disease may be myocardial disorder, primary cardiac arrest, ischemic heart failure, hypertension, ischemic heart disease, coronary artery disease, angina, myocardial infarction, atherosclerosis, or arrhythmia.

The vascular calcification encompasses the calcification of coronary arteries, aorta, and other blood vessels, and an example thereof may be medial calcification or atherosclerotic calcification.

The medial calcification may be used in the same meaning as medial wall calcification or Moenckeberg's sclerosis, and refers to the calcification by calcium deposited in the medial wall. Such medial calcification is known to occur by the expression of bone formation stimulating factors in blood vessels due to diabetes, abnormal calcium metabolism, kidney diseases, or the like.

The atherosclerotic calcification refers to the calcification occurring in atheromatous plaques along the intimal layer. Such atherosclerotic calcification is known to occur by the deposition of calcium directly on atherosclerotic lesion sites.

The valvular calcification may be, for example, aortic valve calcification.

As used herein, the term "prevention" refers to any action to inhibit or delay the progression of vascular or valvular calcification by administration of the pharmaceutical composition according to the present disclosure.

As used herein, the term "treatment" refers to any action to alleviate or advantageously change symptoms of vascular or valvular calcification by administration of the pharmaceutical composition according to the present disclosure.

As used herein, the pharmaceutically acceptable salt may be prepared by a conventional method in the art, which means, for example, forming a salt from an inorganic acid, such as hydrochloric acid, hydrogen bromide, sulfuric acid, hydrogen sodium sulfate, phosphoric acid, or carbonic acid, or an acid salt from an organic acid, such as formic acid, acetic acid, oxalic acid, benzoic acid, citric acid, tartaric acid, gluconic acid, gentisic acid, fumaric acid, lactobionic acid, salicylic acid, or acetylsalicylic acid (aspirin), or forming a metal salt by reaction with ions of an alkali metal, such as sodium or potassium, or forming a different type of pharmaceutically acceptable salt by reaction with an ammonium ion.

The pharmaceutical composition according to the present disclosure may contain as an active ingredient a 3-aryl-1,2, 4-triazole derivative represented by chemical formula 1 above, and may further contain a pharmaceutically acceptable carrier. The pharmaceutically acceptable carrier is conventionally used in the formation of medicines, and examples thereof may include a saline solution, sterile water, Ringer's solution, buffered saline, cyclodextrin, a dextrose solution, a maltodextrin solution, glycerol, ethanol, liposomes, and the like, but are not limited thereto. The pharmaceutical composition may further contain, if necessary, other conventional additives, such as an antioxidant and a buffer solution. In addition, the pharmaceutical composition may be formulated into an injectable formulation, such as an aqueous solution, a suspension, or an emulsion, a pill, a capsule, granules, or a tablet by further adding to a diluent, a dispersant, a surfactant, a binder, a lubricant, and the like thereto. Suitable pharmaceutically acceptable carriers and the formulation thereof may be preferably prepared according to each ingredient by using a method disclosed in the Remington's literature. The pharmaceutical composition of the present disclosure may be formulated as injections, inhalants, or external preparations for skin, but are not particularly limited thereto.

The pharmaceutical composition of the present disclosure may be administered orally or parenterally (for example, intravenous, subcutaneous, intraperitoneal, or topical application) according to a desired method, and the dose thereof depends on the condition and body weight of a patient, severity of disease, drug form, and route and time of administration, but may be appropriately selected by a person skilled in the art.

The pharmaceutical composition of the present disclosure is administered at a pharmaceutically effective amount. As used herein, the term "pharmaceutically effective amount" refers to an amount sufficient to treat a disease at a reasonable benefit/risk ratio applicable to medical treatment, and the level of effective dose may be determined depending on factors including the type and severity of a disease of a patient, activity of drugs, sensitivity to drugs, time of administration, route of administration, and rate of excretion, duration of treatment, and drugs used simultaneously, and other factors that are well known in the field of medicine. The pharmaceutical composition according to the present disclosure may be administered as an individual treatment agent or administered in combination with another treatment agents, and may be administered sequentially or simultaneously with conventional treatment agents, and may be administered single or multiple doses. It is important to administer such an amount that a maximum effect could be attained through a minimum amount without side effects, in consideration of all the above factors, and such an amount can be easily determined by a person skilled in the art.

Specifically, the effective amount of the pharmaceutical composition of the present disclosure may vary depending on the age, sex, condition, and body weight of a patient, absorption of active ingredients in the body, the inactivation rate and excretion rate, the type of disease, and the drug to be used in combination. In general, 0.001-150 mg, and preferably 0.01-100 mg per 1 kg of body weight may be administered daily or every other day, or divided into 1 to 3 times a day. However, the dose may be increased or decreased according to the route of administration, the severity of obesity, sex, body weight, age, and the like, and thus the dose does not limit the scope of the present disclosure by any method.

In accordance with another aspect of the present invention, there is provided a food composition containing a thiamine derivative represented by chemical formula 1 below and a salt thereof for alleviating vascular or valvular calcification:

[Chemical Formula 1]

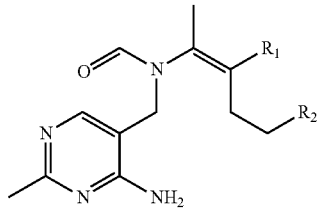

wherein, $R_1$ is any one selected from the group consisting of

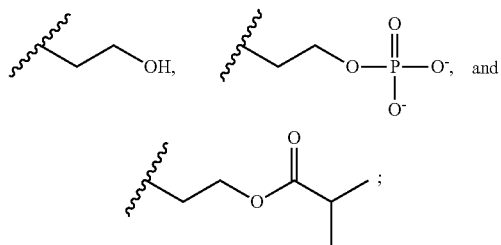

and $R_2$ is any one selected from the group consisting of

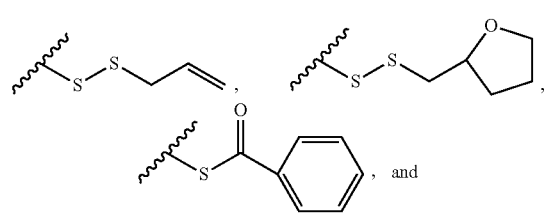

-continued

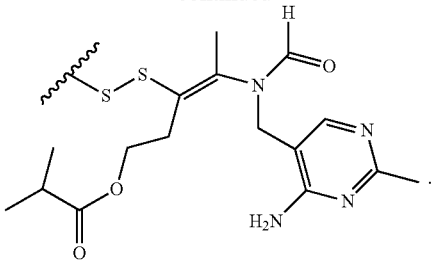

In an embodiment of the present disclosure, $R_1$ may be

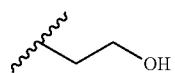 [SMILES: *CCO]

and $R_2$ may be

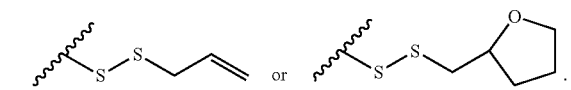

Since the chemical formula 1 in the food composition is the same as that in the foregoing pharmaceutical composition for preventing or treating vascular or valvular calcification, the description of overlapping contents therebetween will be omitted to avoid excessive complexity of the present specification.

The food composition of the present disclosure may be prepared in the form of a powder, granules, a tablet, a capsule, a beverage, or the like. Examples thereof are various types of foods (such as candies), beverages, gums, teas, vitamin complexes, health supplement foods, or the like.

The food composition of the present disclosure may contain not only allithiamine, fursultiamine, benfotiamine, or salts thereof, but also ingredients that are usually added in the manufacturing of foods, and contains, for example, proteins, carbohydrates, fats, nutrients, seasoning agents, and flavoring agents. Examples of the carbohydrates are typical sugars, for example, monosaccharides (such as glucose and fructose), disaccharides (such as maltose, sucrose, and oligosaccharides), and polysaccharides (such as dextrin and cyclodextrin); and sugar alcohols, for example, xylitol, sorbitol, and erythritol. As the flavoring agents, natural flavoring agents (thaumatin, stevia extracts (e.g., rebaudioside A, glycyrrhizin, etc.)) and synthetic flavoring agents (saccharin, aspartame, etc.) may be used. For example, when the food composition of the present disclosure is prepared as a drink, citric acid, liquid fructose, sugar, glucose, acetic acid, malic acid, fruit juice, a Eucommia bark extract, a jujube extract, a licorice extract, in addition to allithiamine, fursultiamine, benfotiamine, or salts thereof, may be further added.

In accordance with another aspect of the present invention, there is provided a method for preventing or treating vascular or valvular calcification, the method including a step of administering to an individual a pharmaceutical composition containing a thiamine derivative or a pharmaceutically acceptable salt thereof.

The individual refers to a subject in need of treatment of a disease, and more specifically, refers to a mammal, such as a human or non-human primate, a mouse, a dog, a cat, a horse, or cattle.

In accordance with still another aspect of the present invention, there is a use of a pharmaceutical composition containing a thiamine derivative or a pharmaceutically acceptable salt thereof for the treatment of vascular or valvular calcification.

The description of overlapping contents with respect to the composition will be omitted considering the complexity of the present specification.

Advantageous Effects

The present disclosure is directed to: a pharmaceutical composition containing a thiamine derivative or a pharmaceutically acceptable salt thereof for preventing or treating vascular or valvular calcification; and a food composition containing a thiamine derivative or a salt thereof for alleviating vascular or valvular calcification, and the compositions of the present disclosure can be helpfully used for preventing, treating, or alleviating vascular or valvular calcification.

MODE FOR CARRYING OUT THE INVENTION

Hereinafter, the present disclosure will be described in more detail with reference to examples. These examples are provided only for the purpose of illustrating the present disclosure in more detail, and therefore, according to the purpose of the present disclosure, it would be apparent to a person skilled in the art that these examples are not construed to limit the scope of the present disclosure.

Preparation Example 1: Primary Culture of Vascular Smooth Muscle Cells (VSMCs)

The surrounding tissues were removed from the thoracoabdominal aorta isolated from male cattle, and endothelial cells that line blood vessels were removed. The cleaned blood vessels were divided into small fragments, which were then aligned on a culture dish containing Dulbecco's modified Eagle's medium (DMEM, Low Glucose, Thermo Fisher Scientific, USA) supplemented with 20% fetal bovine serum (FBS, Hyclone, Australia). Thereafter, culturing was performed in a cell incubator at 37° C. and 5% CO2 for 3-4 weeks. The vascular smooth muscle cells stretching out around the vascular tissues were subjected to primary culture with media changed every two days.

Preparation Example 2: Calcification Induction in Vascular Smooth Muscle Cells

The vascular smooth muscle cells cultured in Preparation Example 1 above were stabilized by subculture in DMEM (high glucose) supplemented with penicillin/streptomycin antibiotics and 10% FBS. Thereafter, the cells were inoculated at $4 \times 10^5$ in 6-well culture dishes, and on the next day of inoculation, the cells were treated with inorganic phosphate (Pi) or both inorganic phosphate and thiamine (fursultiamine or allithiamine; 100 or 200 μM). The cells were cultured for 10 days while media and drugs were changed every 48 hours.

Test Example 1: Investigation of Calcification of Vascular Smooth Muscle Cells

After the induction of calcification by the method in Preparation Example 2 above, the media were removed from the culture dishes, followed by washing with phosphate buffer saline (PBS) three times. Then, 4% paraformaldehyde was added, and the cells were fixed at 4° C. for 15 minutes. After the fixation, the cells were washed with primary distilled water for 5 minutes two times, treated with 5% silver nitrate, and then irradiated with ultraviolet light for 20-30 minutes. Thereafter, the cells were washed with primary distilled water two or three times, and then were determined for a degree of calcification through an optical microscope (BX53 microscope, Olympus, Japan).

Figure 1:
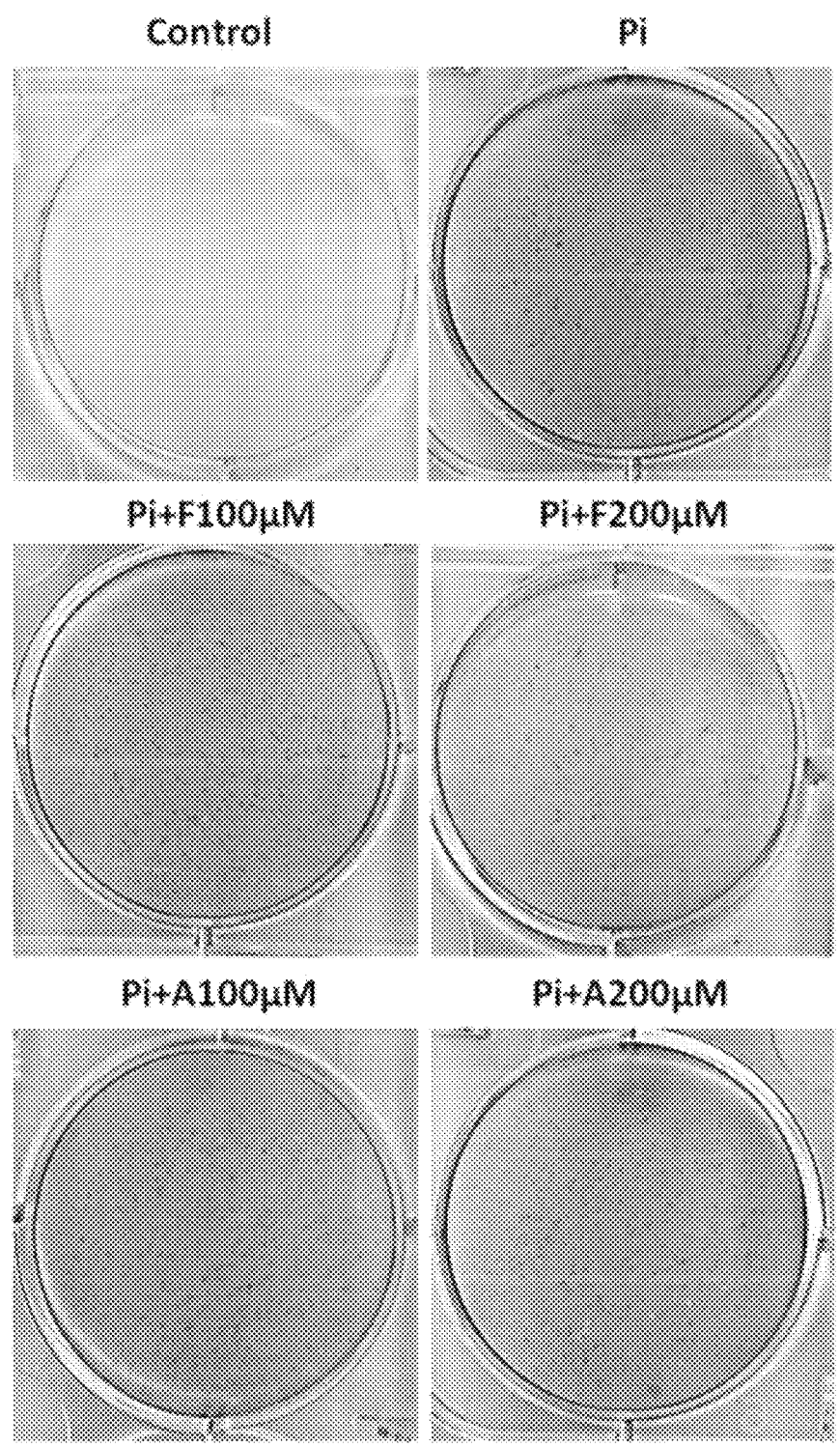
FIG. 1 shows calcification inhibitory effects by fursultiamine (F) and allithiamine (A) according to an example of the present disclosure.

As can be confirmed in FIG. 1, the calcification (black dots) was increased in the vascular smooth muscle cells treated with only inorganic phosphate (Pi), but the calcification (black dots) was inhibited in the vascular smooth muscle cells treated with both fursultiamine (F) and allithiamine (A) at 100 and 200 μM for each (Pi+F100 μM, Pi+F200 μM, Pi+A100 μM, and Pi+A200 μM).

Test Example 2: Quantification of Calcium in Vascular Smooth Muscle Cells

After the induction of calcification by the method in Preparation Example 2 above, the media were removed from the culture dishes, followed by washing with PBS. Then, the cells were decalcified by treatment with 0.6 N HCl at 4° C. for 24 hours, The supernatant was recovered for the use in the quantification of calcium, and proteins were extracted from the cells by using 0.1 N NaOH/0.1% SDS, and quantified by using the BCA method.

The absorbance of a calcium sample (standard) was measured at 612 nm by using a Quantichrom™ calcium analysis kit (DICA-500, BioAssay System, USA), and the calcium concentration was determined by using Equation 1, and then, the value thereof was divided (corrected) by the quantified amount of proteins, thereby finally quantifying calcium.

$$\text{Calcium concentration} = \frac{OD_{SAMPLE} \backslash - OD_{BLANK}}{\text{Slope}} (mg/dL). \quad \text{[Equation 1]}$$

($OD_{SAMPLE}$ and $OD_{BLANK}$ represent the $OD_{612nm}$ values of calcium sample and blank (water), respectively; and the slope represents the inclination value on the measured absorbance graph)

Figure 2:
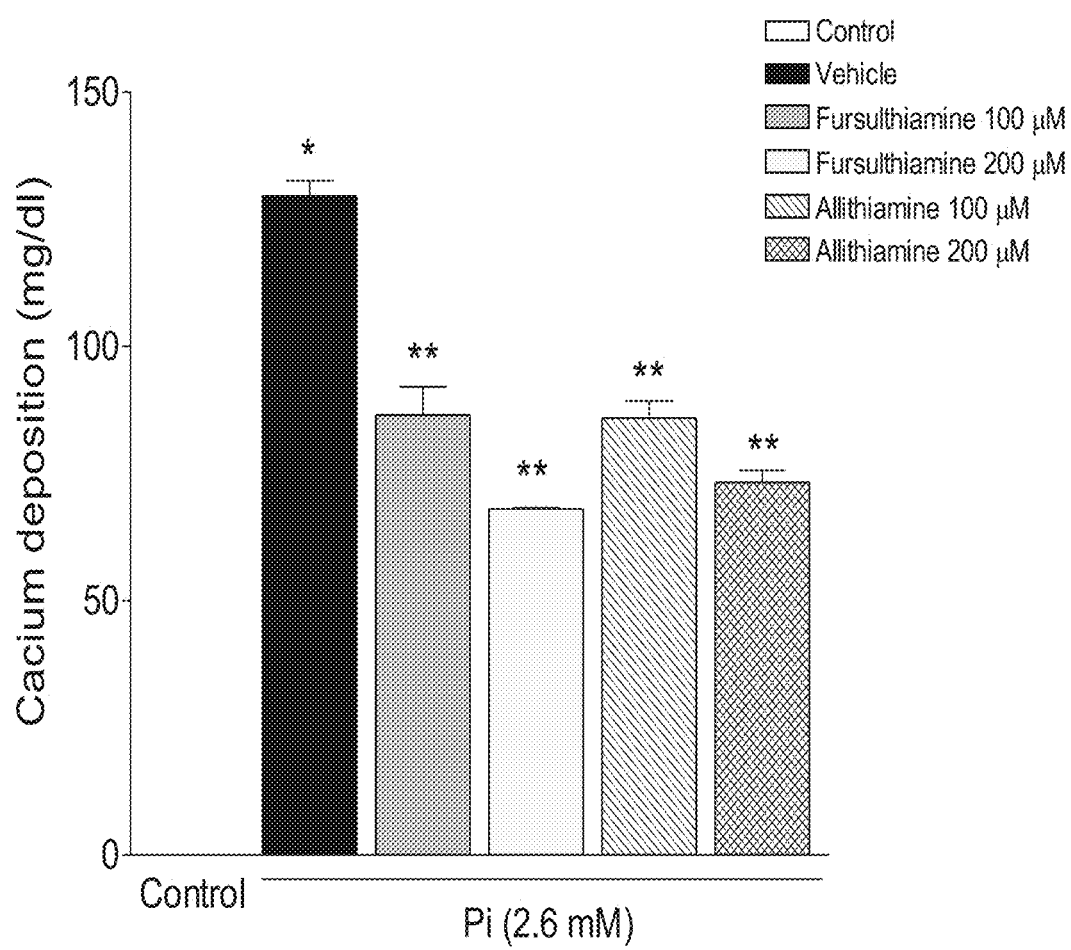
FIG. 2 shows the quantification of calcified calcium in order to investigate the calcification inhibitory effects by fursultiamine and allithiamine according to an example of the present disclosure.

As can be confirmed from FIG. 2, the calcium amount was increased by inorganic phosphate in the vascular smooth muscle cells treated with only inorganic phosphate (vehicle), but the calcium amount increased by inorganic phosphate was decreased by treatment with both fursultiamine and allithiamine at 100 and 200 μM for each (*p<0.01 vs Control; **p<0.01 vs Vehicle).

Test Example 3: In Vivo

C57BL/6J mice aged 8-9 weeks were grouped into 5 groups of 7 mice each, and four groups (one group being used as a control) underwent the induction of vascular calcification by subcutaneous administration of a high dose ($9.0 \times 10^5$ IU) of vitamin D3 (Vit. D3) once a day for a total of 3 days.

Out of these, three groups were subjected to oral administration of 10 mg/kg and 30 mg/kg fursultiamine and 50 mg/kg dichloroacetate (DCA, positive control), respectively, from three days before the first administration of vitamin D3, once a day for a total of 13 days.

3-1. Von Kossa Staining

First, on the 10th day after the administration of vitamin D3, the mice were sacrificed and the abdomen was opened, and then the aorta was separated by cleanly removing surrounding tissues of the aorta, and fixed with 4% paraformaldehyde (PFA) for 24 hours. The fixed aorta was washed, immersed in a 5% silver nitrate solution, and incubated under UV light for 30 minutes.

Figure 3:
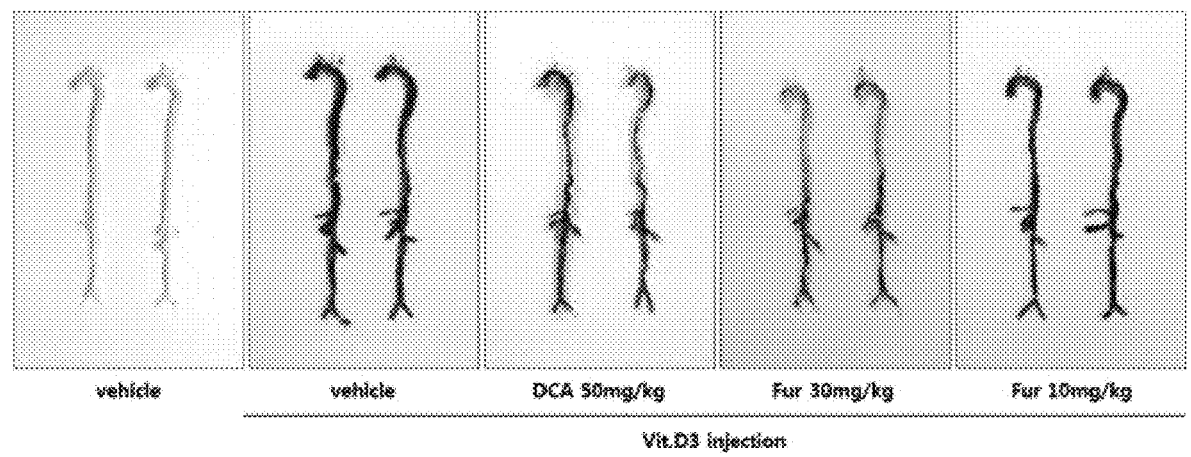
FIG. 3 shows the results of Von Kossa staining executed in order to investigate the calcification inhibitory effect (in vivo) by fursultiamine according to an example of the present disclosure.

As can be confirmed from FIG. 3, the aorta was mostly darkly colored due to an increase in vascular calcification in the vitamin D3 groups, whereas the colored parts were significantly reduced in the DCA group (positive control) compared with the vehicle group. The colored parts were also reduced (recovered) dose-dependently in the fursultiamine groups of the present disclosure, and especially, the degree of recovery was excellent in the 30 mg/kg administration group compared with the DCA administration group (positive control).

3-2. Calcium Quantification

Additionally, on the 10th day after the administration of vitamin D3, the mice were sacrificed and the abdomen was opened, and then the aorta was separated by cleanly removing surrounding tissues and frozen in liquid nitrogen. The frozen tissues were thawed, weighed after the removal of moisture, and then subjected to decalcification with a 0.6 N HCl solution. The colorimetric Ca quantification kit (Bioassay DICA-500) was used to quantify calcium in the 0.6 N HCl solution used in the decalcification, and the calcium quantification was corrected by using the tissue weight.

Figure 4:
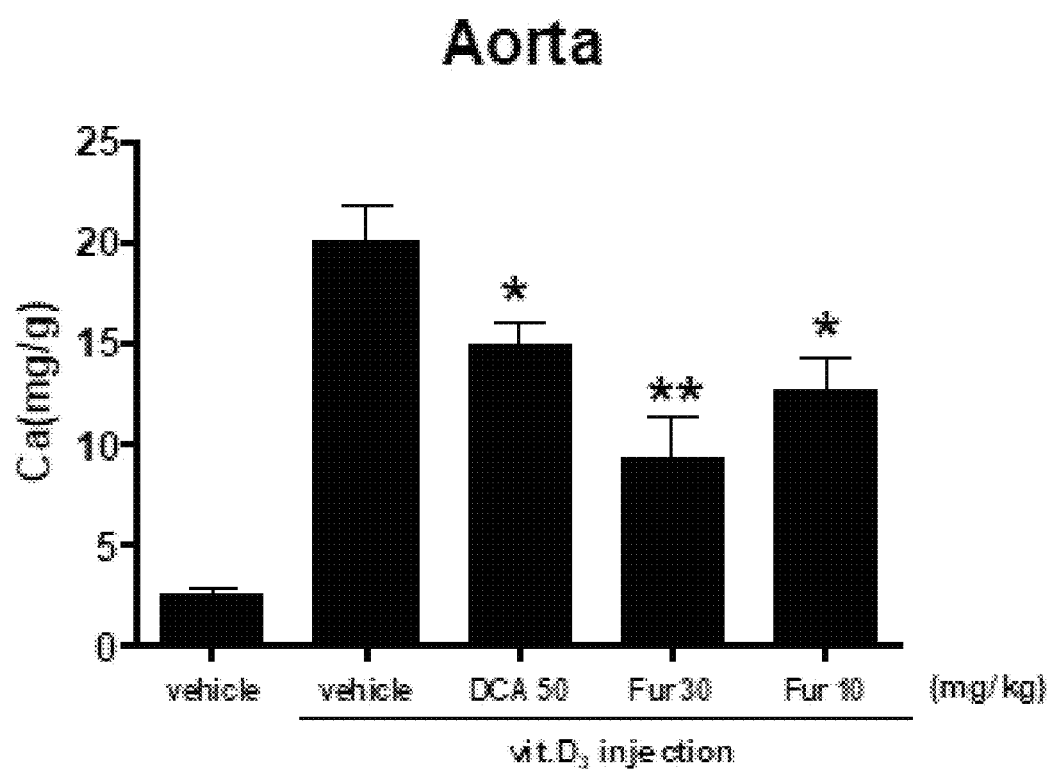
FIG. 4 shows the quantification of calcium deposited in blood vessels in order to investigate the calcification inhibitory effect (in vivo) by fursultiamine according to an example of the present disclosure.

As can be confirmed from FIG. 4, the amount of calcium was increased by about 10 times in the vitamin D3 groups compared with the control group with no vitamin D3 injection, but the amount of calcium in the aorta, which increased by vitamin D3, was significantly decreased in the DCA group (positive control). The amount of calcium was also decreased dose-dependently in the fursultiamine groups of the present disclosure, and the degrees of decrease were excellent compared with the DCA group (positive control).

The invention claimed is:

1. A method for preventing or treating vascular calcification or valvular calcification in a subject, the method comprising:
    a step of administering to the subject a pharmaceutical composition comprising a thiamine derivative represented by chemical formula 1, below, or a pharmaceutically acceptable salt thereof,

[Chemical Formula 1]

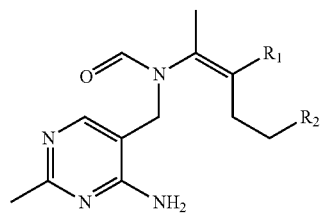

wherein,

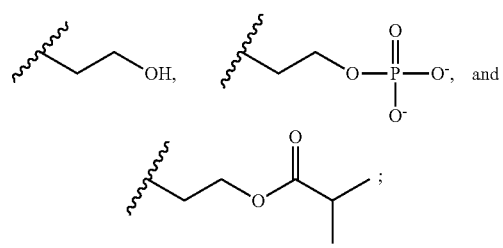

$R_1$ is selected from the group consisting of
and
$R_2$ is selected from the group consisting of

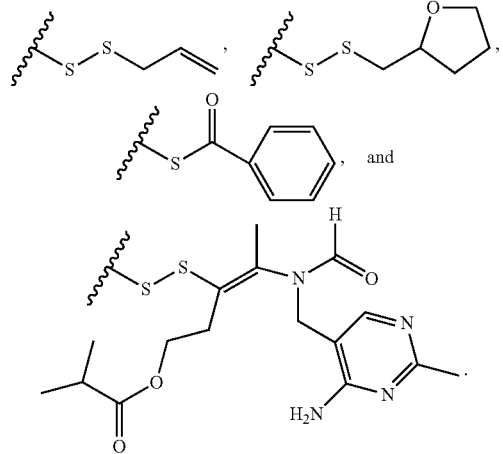

2. The method of claim 1, wherein $R_1$ is

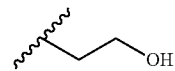 [SMILES: *CCO]

and $R_2$ is

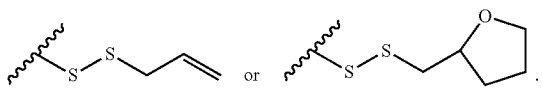

3. The method of claim 1, wherein the vascular or valvular calcification is caused by at least one disease or condition selected from the group consisting of a valvular disease, hyperlipidemia, aging, estrogen deficiency, angina, heart failure, kidney disease, uremia, diabetes, an inflammatory disease, and a cardiovascular disease.

4. The method of claim 1, wherein the vascular calcification is medial calcification or atherosclerotic calcification.

5. The method of claim 1, wherein the valvular calcification is aortic valve calcification.

* * * * *